(12) United States Patent
Nilsen et al.

(10) Patent No.: US 10,709,798 B2
(45) Date of Patent: Jul. 14, 2020

(54) CRYSTALLIZATION PROCESS OF TRICYCLIC INDOLE DERIVATIVES

(71) Applicant: GE Healthcare Limited, Buckinghamshire (GB)

(72) Inventors: Sondre Nilsen, Nydalen (NO); Srinath Balaji Aralikatti Prahladachar Balaji, Harapanahali (IN); Umamaheshwar P. Mokkapati, Secunderabad (IN); Afsal Mohammed Kadavilpparampu Mohamed, Bangalore (IN)

(73) Assignee: GE HEALTHCARE LIMITED, Buckinghamshire (GB)

( * ) Notice: Subject to any disclaimer, the term of this patent is extended or adjusted under 35 U.S.C. 154(b) by 0 days.

(21) Appl. No.: 14/648,353

(22) PCT Filed: Nov. 28, 2013

(86) PCT No.: PCT/EP2013/074986
§ 371 (c)(1),
(2) Date: May 29, 2015

(87) PCT Pub. No.: WO2014/083113
PCT Pub. Date: Jun. 5, 2014

(65) Prior Publication Data
US 2015/0335766 A1    Nov. 26, 2015

(30) Foreign Application Priority Data

Nov. 30, 2012   (IN) .......................... 3689/DEL/2012
Jan. 15, 2013   (GB) ................................. 1300647.3

(51) Int. Cl.
| | | |
|---|---|---|
| *A61B 5/00* | (2006.01) | |
| *A61B 8/00* | (2006.01) | |
| *A61B 10/00* | (2006.01) | |
| *A61K 49/00* | (2006.01) | |
| *C07D 209/88* | (2006.01) | |

(52) U.S. Cl.
CPC ........ *A61K 49/0017* (2013.01); *C07D 209/88* (2013.01)

(58) Field of Classification Search
CPC .......................... A61K 49/0017; C07D 209/88
USPC ......................................................... 424/9.6
See application file for complete search history.

(56) References Cited

U.S. PATENT DOCUMENTS

| | | | |
|---|---|---|---|
| 6,177,440 B1 * | 1/2001 | Bach et al. .................... | 514/292 |
| 8,501,153 B2 * | 8/2013 | Achanath et al. ........... | 424/1.11 |
| 8,790,619 B2 * | 7/2014 | Wadsworth et al. ........ | 424/1.11 |
| 9,061,996 B2 | 6/2015 | Mantzilas et al. | |
| 9,168,317 B2 | 10/2015 | Jones | |
| 9,220,795 B2 * | 12/2015 | Wadsworth et al. | |
| 9,314,541 B2 | 4/2016 | Jones | |
| 2011/0070161 A1 * | 3/2011 | Achanath et al. ........... | 424/1.89 |

FOREIGN PATENT DOCUMENTS

| | | |
|---|---|---|
| EP | 0952149 B1 | 6/2004 |
| EP | 2618850 A1 | 7/2013 |
| EP | 2621544 A1 | 8/2013 |
| EP | 2943195 A1 | 11/2015 |
| EP | 2651857 B1 | 2/2017 |
| EP | 2411362 B1 | 5/2017 |
| JP | 2012-521973 A | 9/2012 |
| JP | 2012521973 A | 9/2012 |
| JP | 2013-538818 A | 10/2013 |
| JP | 2014-506874 A | 3/2014 |
| JP | 5651163 B2 | 1/2015 |
| JP | 5932804 B2 | 6/2016 |
| WO | 1999/025340 A1 | 5/1999 |
| WO | 2003/014082 A1 | 2/2003 |
| WO | 2003/016277 A1 | 2/2003 |
| WO | 2010109007 A2 | 9/2010 |
| WO | 2011/117421 A1 | 9/2011 |
| WO | 2012/038532 A1 | 3/2012 |
| WO | 2012041953 A1 | 4/2012 |
| WO | 2012080349 A1 | 6/2012 |
| WO | 2014/083113 A1 | 6/2014 |

OTHER PUBLICATIONS

Kim et al. Nucl. Med. Biol. 36 (2009) 323-334.*
Harry Wadsworth et al, "[18F]GE-180: A novel fluorine-18 labelled PET tracer for imaging Translocator protein 18kDA (TSPO)", Bioorganic & Medicinal Chemistry Letters, vol. 22, No. 3, Feb. 1, 2012, pp. 1308-1313.
International Search Report dated Feb. 7, 2014 which was issued in connection with PCT Patent Application No. PCT/EP2013/074986 which was filed on Nov. 28, 2013.
GB Search Report dated May 14, 2013 which was issued in connection with GB Patent Application No. 1300647.3 which was filed on Jan. 15, 2013.
Search Report in corresponding Chinese Appl. No. 201380062872.4 dated Jun. 1, 2016. (English translation enclosed—CN102448933A equivalent to previously filed WO2010/109007).
Office Action in corresponding Chinese Appl. No. 201380062872.4 dated Jun. 1, 2016. (English translation is enclosed and Application Form Translation).
Wadsworth et al. "Supporting Information [ 18 F]GE-180: A Novel Fluorine-18 labelled PET Tracer for Imaging Translocator Protein 18kDa (TSPO)", Bioorganic & Medicinal Chemistry Letters, Dec. 27, 2011, pp. 18-7.
Davies et al., "Mapping the Melatonin Receptor. 5. Melatonin Agonists and Antagonists Derived From Tetrahydrocyclopent[b]indoles, Tetrahydrocarbazoles and Hexahydrocyclohept[b]indoles", Journal of Medicinal Chemistry,vol. 41, Issue-4, 1998, pp. 451-467.

(Continued)

*Primary Examiner* — Michael G. Hartley
*Assistant Examiner* — Sean R Donohue
(74) *Attorney, Agent, or Firm* — Culhane Meadows PLLC; Jeff B. Vockrodt

(57) ABSTRACT

A composition comprising a tricyclic indole compound. The composition has a higher purity and better impurity profile than known compositions comprising said tricyclic indole compound and as a consequence has superior properties, particularly when said compound is destined for use in vivo as a therapeutic or diagnostic agent.

5 Claims, No Drawings

(56) References Cited

OTHER PUBLICATIONS

Julia et al., "Bulletin De La Societe De France", 1962, pp. 2262-2263.

Satyamurthy et al., "Electronic Generators for the Production of Positron-Emitter Labeled Radiopharmaceuticals: Where Would PET Be Without Them?", Clinical Positron Imaging, vol. 2, Issue-5, 1999, pp. 233-253.

Wuts et al., "Protective Groups in Organic Synthesis", In book: Greene's Protective Groups in Organic Synthesis, Fourth Edition, John Wiley & Sons, 2007.

International Preliminary Report on Patentability Received for PCT Patent Application No. PCT/EP2013/074986, dated Jun. 11, 2015, 6 pages.

Office Action Received for Japanese Patent Application No. 2015-544462, dated Aug. 1, 2017, 11 pages (5 Pages of English Translation + 6 Pages of official Copy).

Wadsworth, H., et al., "[18F]GE-180: A novel fluorine-18 labelled PET tracer for imaging Translocator protein 18 kDa (TSPO)", Bioorganic & Medicinal Chemistry Letters, vol. 22, published 2012, pp. 1308-1313.

\* cited by examiner

CRYSTALLIZATION PROCESS OF TRICYCLIC INDOLE DERIVATIVES

CROSS-REFERENCE TO RELATED APPLICATIONS

This is a national stage application under 35 U.S.C. § 371(c) of prior filed, co-pending PCT application serial number PCT/EP2013/074986, filed on Nov. 28, 2013, which claims priority to Indian Patent Application Serial No. 3689/DEL/2012 filed Nov. 30, 2012 and titled CRYSTALLIZATION and Great Britain Patent Application Serial No. 1300647.3 filed Jan. 15, 2013 and titled CRYSTALLIZATION. All of the above-listed applications are herein incorporated by reference.

TECHNICAL FIELD OF THE INVENTION

Embodiments of the invention relate to a composition comprising a tricyclic indole compound. More specifically the embodiments of the invention relate to wherein said composition has a more favourable impurity profile as compared with known compositions comprising said compound.

DESCRIPTION OF RELATED ART

Tricyclic indole compounds are known in the art and have been reported to have application variously as melatonin antagonists (Davies 1998 J Med Chem; 41: 451-467), secretory phospholipase A2 inhibitors (Anderson et at EP 0952149 A1), treatment for Alzheimer's disease (Wantanabe WO 99/25340), treatment of inflammatory diseases such as septic shock (Kinnick et at WO 03/014082 and WO 03/016277) and binders of high affinity to translocator protein (TSPO, formerly known as peripheral benzodiazepine receptor; Wadsworth et at (WO 2010/109007).

The synthesis of these tricyclic indole compounds comprises a condensation reaction between an analine and a bromo oxocycloalkanecarboxylate, followed by cyclization in the presence of a zinc halide. One problem with this cyclization reaction is that more than one cyclized isomer can result, as illustrated in Scheme 1 below:

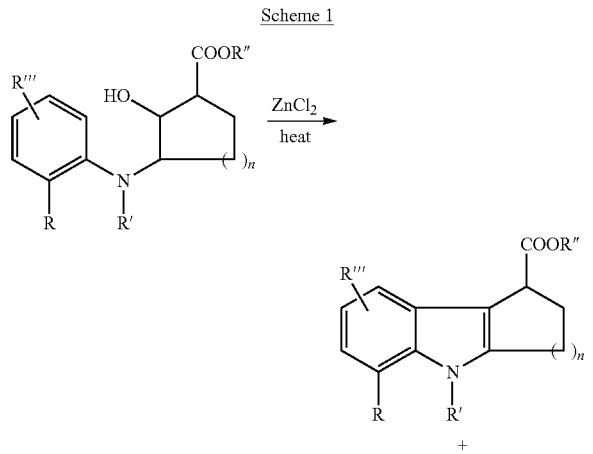

Scheme 1

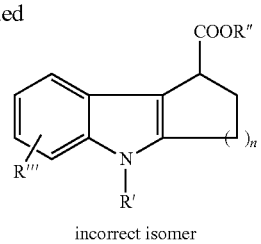

incorrect isomer

The incorrect isomer is formed when the R group reacts with the —OH. This incorrect isomer has similar reactivity to the correct isomer and as a consequence when any further steps are taken to modify the correct isomer, a respective incorrect isomer is generated in the reaction mixture. This is particularly problematic if the resultant compound is intended for in vivo use, as the incorrect isomer will likely compete with the correct isomer for binding to the intended biological target.

In the method described by Kinnick et at (WO 03/014082), a chloro group was introduced at the R position illustrated in Scheme 1 with the aim of forcing the cyclization reaction to take place in just one way and result in only the correct cyclized isomer. This strategy was applied by Wadsworth et at (WO 2010/109007) in the cyclization reaction illustrated in Scheme 2 below (where Et=ethyl and Bz=benzyl):

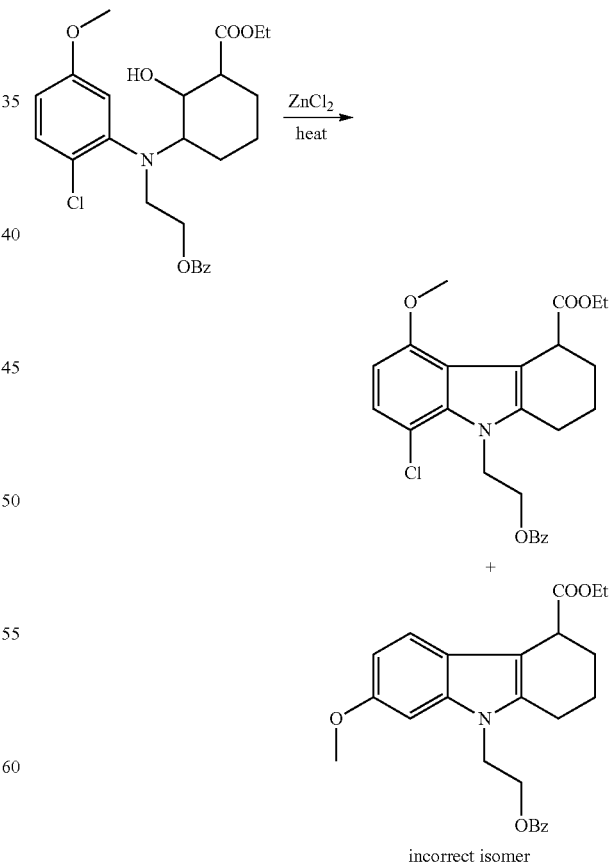

Scheme 2 incorrect isomer

Work up and chromatographic purification of the resultant reaction mixture was followed by removal of the chloro group and conversion of the ethyl to diethyl amine to obtain a key intermediate, which in turn was purified using crystallization from diethyl ether. Purity of the key intermediate was still only 71%. When investigating this particular reaction, the present inventors have found that the purified reaction mixture still contains an amount of the incorrect isomer, which is evidently difficult to remove.

There is therefore a need for a method to obtain these and similar tricyclic indole compounds where the amount of incorrect isomer is reduced or eliminated.

SUMMARY OF THE INVENTION

Embodiments of the invention relate to a composition comprising a tricyclic indole compound wherein the quantity of an incorrect isomer in said composition is reduced. The composition therefore has a higher purity and better impurity profile than known compositions comprising said tricyclic indole compound and as a consequence has superior properties, particularly when said compound is destined for use in vivo as a therapeutic or diagnostic agent. Also provided by the embodiments of the invention is a method to make the composition of the invention, a pharmaceutical composition comprising the composition of the invention, and use of the composition of the invention in a medical method.

DETAILED DESCRIPTION

In one aspect, the present invention provides a composition comprising a compound of Formula I:

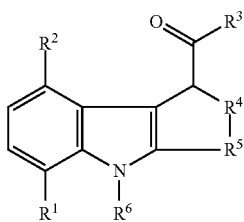

wherein:

$R^1$ is hydrogen, $C_{1-3}$ alkyl, $C_{1-3}$ alkoxy, or halo;

$R^2$ is hydroxyl, halo, cyano, $C_{1-3}$ alkyl, $C_{1-3}$ alkoxy, $C_{1-3}$ fluoroalkyl, or $C_{1-3}$ fluoroalkoxy;

$R^3$ is —N—$R^7R^8$ wherein $R^7$ and $R^8$ are hydrogen, $C_{1-6}$ alkyl, $C_{7-10}$ arylalkyl or, together with $R^7$, forms a nitrogen-containing $C_{4-6}$ aliphatic ring;

$R^4$ is O, S, SO, $SO_2$ or $CH_2$;

$R^5$ is $CH_2$, $CH_2$—$CH_2$, $CH(CH_3)$—$CH_2$ or $CH_2$—$CH_2$—$CH_2$;

$R^6$ is -$A^1$-$R^9$ wherein $A^1$ is a bond or $C_{1-10}$ alkylene, and $R^9$ is hydrogen, fluoro or a leaving group, or $R^9$ is the group —O—$R^{10}$ wherein $R^{10}$ is hydrogen, $C_{1-3}$ alkyl, $C_{3-6}$ aryl, $C_{7-10}$ arylalkyl, or a hydroxyl protecting group, wherein said composition comprises no more than 1% of a compound of Formula II:

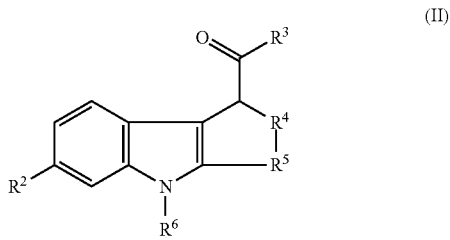

wherein $R^2$ to $R^6$ are as defined for Formula I.

The term "alkyl" used either alone or as part of another group is defined as any straight —$C_nH_{2n+1}$ group, branched —$C_nH_{2n+1}$ group wherein n is >3, or cyclic —$C_nH_{2n-1}$ group where n is >2. Non-limiting examples of alkyl groups include methyl, ethyl, propyl, isobutyl, cyclopropyl and cyclobutyl.

The term "alkoxy" refers to an alkyl group as defined above comprising an ether linkage, and the term "ether linkage" refers to the group —C—O—C—. Non-limiting examples of alkoxy groups include, methoxy, ethoxy, and propoxy.

The term "halo" or "halogen" is taken to mean any one of chloro, fluoro, bromo or iodo.

The term "hydroxyl" refers to the group —OH.

The term "cyano" refers to the group —CN.

The terms "fluoroalkyl" and "fluoroalkoxy" refer respectively to an alkyl group and an alkoxy group as defined above wherein a hydrogen is replaced with a fluoro.

The term "arylalkyl" refers to an aryl-substituted alkylene group wherein "aryl" refers to any molecular fragment or group which is derived from a monocyclic or polycyclic aromatic hydrocarbon, or a monocyclic or polycyclic heteroaromatic hydrocarbon and "alkylene" refers to a divalent linear —$C_nH_{2n}$— group.

A "nitrogen-containing $C_{4-6}$ aliphatic ring" is a saturated $C_{4-6}$ alkyl ring comprising a nitrogen heteroatom. Examples include pyrolidinyl, piperidinyl and morpholinyl rings.

The term "leaving group" refers to a molecular fragment that departs with a pair of electrons in heterolytic bond cleavage. Non-limiting examples of suitable leaving groups include halo groups selected from chloro, iodo, or bromo, aryl or alkyl sulfonates such as tosylate, triflate, nosylate or mesylate.

The term "protecting group" is meant a group which inhibits or suppresses undesirable chemical reactions, but which is designed to be sufficiently reactive that it may be cleaved from the functional group in question to obtain the desired product under mild enough conditions that do not modify the rest of the molecule. Protecting groups are well-known in the art and are discussed in detail in 'Protective Groups in Organic Synthesis', by Greene and Wuts (Fourth Edition, John Wiley & Sons, 2007). Non-limiting examples of suitable protecting groups for hydroxyl include acetyl (—$COCH_3$), benzoyl (—$COC_6H_5$), benzyl (—$CH_2C_6H_5$), β-methoxyethoxymethyl ether (MEM), dimethoxytrityl (DMT) and methoxymethyl ether (MOM).

In a first embodiment $R^1$ is halo and in a second embodiment $R^1$ is hydrogen. When $R^1$ is halo it is more particularly chloro or bromo, and more particularly chloro.

In an embodiment $R^2$ is halo, $C_{1-3}$ alkoxy or $C_{1-3}$ fluoroalkoxy, more particularly hydrogen, halo or $C_{1-3}$ alkoxy, more particularly hydrogen, fluoro or methoxy, and more particularly methoxy.

In an embodiment, $R^3$ is —N—$R^7R^8$ wherein $R^7$ and $R^8$ are $C_{1-6}$ alkyl or $C_{7-10}$ arylalkyl, more particularly wherein $R^7$ and $R^8$ are $C_{1-3}$ alkyl, more particularly wherein $R^7$ and $R^8$ are both ethyl.

In an embodiment $R^4$ is $CH_2$.

In an embodiment, $R^5$ is $CH_2$—$CH_2$.

In a first embodiment, $R^6$ is -$A^1$-$R^9$ wherein $A^1$ is $C_{1-10}$ alkylene, most particularly $C_{1-3}$ alkylene and more particularly ethylene, and $R^9$ is the group —O—$R^{10}$ wherein $R^{10}$ is $C_{7-10}$ arylalkyl or a hydroxyl protecting group, more particularly wherein $R^{10}$ is a hydroxyl protecting group.

In a second embodiment $R^6$ is -$A^1$-$R^9$ wherein $A^1$ is $C_{1-10}$ alkylene, more particularly $C_{1-3}$ alkylene and more particularly ethylene, and $R^9$ is hydrogen, fluoro or a leaving group. Where $R^9$ is fluoro it is [$^{18}$F]fluoro, such that the composition of the invention is an "in vivo imaging composition". Where $R^9$ is a leaving group the composition of the invention is a "precursor composition" that can be reacted with [$^{18}$F]fluoride to obtain the in vivo imaging composition. The leaving group is, in an embodiment, halo, or an aryl or alkyl sulfonate, more particularly an aryl or alkyl sulfonate, and more particularly tosylate, triflate, nosylate or mesylate.

The term "no more than" should be understood to mean any amount less than the quoted percent quantity. Therefore no more than 1% means any amount between 0-1%. In an embodiment of the composition of the present invention there is 0% of said compound of Formula II in the composition of the invention. However, in reality, it may be that at least a trace amount of the compound of Formula II remains in the composition, i.e. no more than 1% could e.g. refer to 0.1-1%.

In a first composition of an embodiment of the present invention:

$R^1$ is halo, more particularly chloro or bromo, and more particularly chloro;

$R^2$ is halo, $C_{1-3}$ alkoxy or $C_{1-3}$ fluoroalkoxy, more particularly hydrogen, halo or $C_{1-3}$ alkoxy, more particularly hydrogen, fluoro or methoxy, and more particularly methoxy;

$R^3$ is —N—$R^7R^8$ wherein $R^7$ and $R^8$ are $C_{1-6}$ alkyl or $C_{7-10}$ arylalkyl, more particularly wherein $R^7$ and $R^8$ are $C_{1-3}$ alkyl, more particularly wherein $R^7$ and $R^8$ are both ethyl;

$R^4$ is $CH_2$;

$R^5$ is $CH_2$—$CH_2$; and, $R^6$ is -$A^1$-$R^9$ wherein $A^1$ is $C_{1-10}$ alkylene, more particularly $C_{1-3}$ alkylene and more particularly ethylene, and $R^9$ is the group —O—$R^{10}$ wherein $R^{10}$ is $C_{7-10}$ arylalkyl or a hydroxyl protecting group, more particularly wherein $R^{10}$ is a hydroxyl protecting group.

In a second composition of an embodiment of the present invention:

$R^1$ is hydrogen;

$R^2$ is halo, $C_{1-3}$ alkoxy or $C_{1-3}$ fluoroalkoxy, more particularly hydrogen, halo or $C_{1-3}$ alkoxy, more particularly hydrogen, fluoro or methoxy, and more particularly methoxy;

$R^3$ is —N—$R^7R^8$ wherein $R^7$ and $R^8$ are $C_{1-6}$ alkyl or $C_{7-10}$ arylalkyl, more particularly wherein $R^7$ and $R^8$ are $C_{1-3}$ alkyl, more particularly wherein $R^7$ and $R^8$ are both ethyl;

$R^4$ is $CH_2$;

$R^5$ is $CH_2$—$CH_2$; and, $R^6$ is -$A^1$-$R^9$ wherein $A^1$ is $C_{1-10}$ alkylene, more particularly $C_{1-3}$ alkylene and more particularly ethylene, and $R^9$ is hydrogen, fluoro, or a leaving group, more particularly wherein $R^9$ is fluoro or a leaving group, wherein said fluoro is [$^{18}$F]fluoro and wherein said leaving group is, in an embodiment, halo, or an aryl or alkyl sulfonate, more particularly an aryl or alkyl sulfonate, and more particularly tosylate, triflate, nosylate or mesylate. This second composition can therefore either be an in vivo imaging composition or a precursor composition.

The compound of Formula I and the compound of Formula II of the composition of the embodiments of the invention as defined above may each comprise a chiral centre. All forms of such isomer, including enantiomers and diastereoisomers, are encompassed by the present invention. The compound of Formula I and the compound of Formula II may be present in the composition of the embodiments of the invention as racemic mixture or as an enantiomerically-enriched mixture, or the racemic mixture may be separated using well-known techniques and an individual enantiomer maybe used alone. In an embodiment, the composition of the invention comprises the S-enantiomer of said compound of Formula I and said compound of Formula II.

In an embodiment, the composition of the present invention comprises no more than 0.5% of said compound of Formula II, more particularly no more than 0.3%, more particularly no more than 0.2%, and more particularly no more than 0.1%.

In a composition according to an embodiment of the present invention, said compound of Formula I is a compound of Formula Ia:

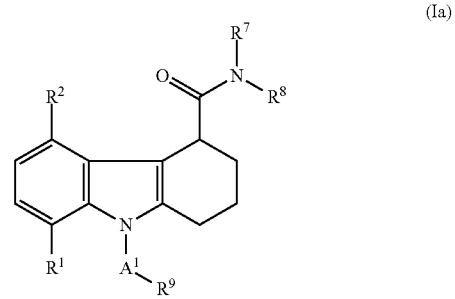

(Ia)

wherein each of $R^1$, $R^2$, $R^7$, $R^8$, $R^9$ and $A^1$ are as variously defined hereinabove, and said compound of Formula II is a compound of Formula IIa:

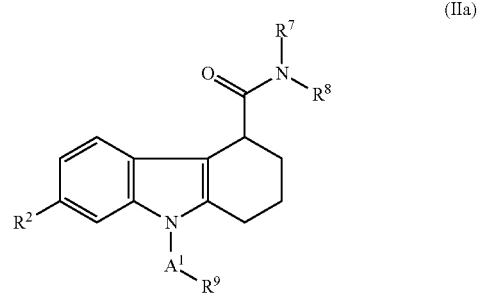

(IIa)

wherein each of $R^2$, $R^7$, $R^8$, $R^9$ and $A^1$ are as variously defined hereinabove.

For a composition according to an embodiment:

$R^1$ is hydrogen;

$R^2$ is fluoro or methoxy;

$R^7$ and $R^8$ are $C_{1-6}$ alkyl;

$R^9$ is hydrogen, fluoro or a leaving group; and,
$A^1$ is $C_{1-10}$ alkylene.

For a composition according to an embodiment:
$R^1$ is hydrogen;
$R^2$ is methoxy;
$R^7$ and $R^8$ are $C_{1-3}$ alkyl;
$R^9$ is [$^{18}$F]fluoro or an aryl or alkyl sulfonate; and,
$A^1$ is $C_{1-3}$ alkylene.

For a composition according to an embodiment:
$R^1$ is hydrogen;
$R^2$ is methoxy;
$R^7$ and $R^8$ are methyl or ethyl;
$R^9$ is [$^{18}$F]fluoro, tosylate, triflate, nosylate or mesylate; and,
$A^1$ is $C_{1-3}$ alkylene.

For a composition according to an embodiment:
$R^1$ is hydrogen;
$R^2$ is methoxy;
$R^7$ and $R^8$ are both ethyl;
$R^9$ is [$^{18}$F]fluoro or mesylate; and,
$A^1$ is ethylene.

Where an above-defined composition of embodiment of the invention comprises $^{18}$F it is an in vivo imaging composition, and where it comprises a leaving group, it is a precursor composition.

In another aspect, the present invention comprises a method to obtain the composition as defined hereinabove wherein said method comprises crystallization of a reaction mixture comprising said compound of Formula I as defined hereinabove, and said compound of Formula II as defined hereinabove, wherein said crystallization is carried out in a suitable organic solvent in the presence of a catalytic amount of a weak organic base in order to obtain said composition.

The term "catalytic amount" means an amount of a substance used in a chemical reaction as a catalyst and is generally much smaller than the stoichiometric amounts of either reactants or products.

The term "suitable organic solvent" encompasses non-polar solvents and polar aprotic solvents, suitably having a dielectric constant of between 3.5-8. Examples of suitable organic solvents for use in the method of the embodiments of the present invention include diethyl ether, ethyl acetate, tetrahydrofuran (THF) and diisopropylether. Diethyl ether is preferred in some embodiments.

The term "weak organic base" refers to an organic compound which acts as a base. Organic bases are generally proton acceptors and usually contain nitrogen atoms, which can easily be protonated. Amines and nitrogen-containing heterocyclic compounds are organic bases. Non-limiting examples include pyridine, alkyl amines, morpholine, imidazole, benzimidazole, histidine, phosphazene bases and hydroxides of some organic cations. In the context of embodiments of the present invention alkyl amines are preferred, e.g. N,N-diisopropyl amine, triethyl amine or diethyl amine.

The present inventors have found that when using the method of embodiments of the invention a very good quality product is obtained having optimum yield. Please refer to Example 1 wherein a method to obtain the composition according to embodiments of the present invention is described. It can be seen that by applying the method of embodiments of the invention to the purification of a key intermediate in the synthesis, the amount of incorrect isomer remaining is significantly less than when the prior art method for purification of this intermediate is used.

In an embodiment, the reaction mixture for use in the method of the invention is obtained using a method comprising cyclization of a compound of Formula III:

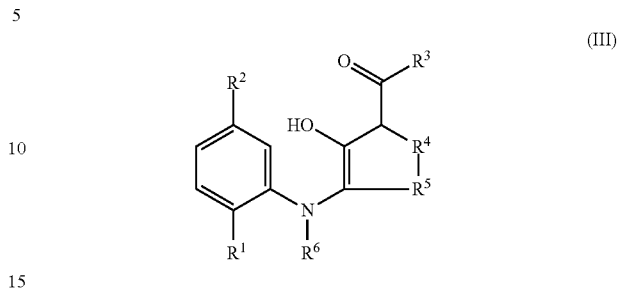

(III)

wherein:
$R^1$ is as suitably and defined hereinabove;
$R^2$ is as suitably and defined hereinabove;
$R^3$ is as suitably and defined hereinabove;
$R^4$ is as suitably and defined hereinabove;
R5 is as suitably and defined hereinabove; and,
$R^5$ is as suitably and defined hereinabove; and,
wherein said cyclization is carried out by reaction of said compound of Formula III with a zinc halide.

In an embodiment, said zinc halide is zinc chloride or zinc bromide, more particularly zinc chloride.

In an embodiment said zinc chloride is added lot-wise. The term "lot-wise" means introduction of a reagent to a reaction using more than one addition. In the context of embodiments of the present invention said more than one addition comprises a first addition and a second addition wherein said second addition is carried out at least 6 hours after said first addition. Said lot-wise addition, in an embodiment, further comprises a third addition wherein said third addition is carried out said second addition.

Cyclization of said compound of Formula III is, in an embodiment, carried out wherein $R^1$ is halogen, more particularly chloro, and wherein $R^6$ comprises a protecting group. This is to ensure that the cyclization reaction results in as much of the correct isomer as possible. The $R^1$ and $R^6$ group can be converted subsequently using methods well-known to the person skilled in the art to obtain other $R^1$ and $R^6$ groups as defined above.

Compounds of Formula III can be obtained from commercial starting materials using or adapting methods described in the prior art. Reference is made in this regard to the teachings of Julia & Lenzi (Bulletin de la Société de France 1962: 2262-2263), Davies et at (J Med Chem 1998; 41: 451-467), Kinnick et at (WO 2003/014082 and WO 2003/016277), Anderson et at (EP0952149 B1) and Wadsworth et at (WO 2010/109007). In each of these publications compounds of Formula III are obtained by condensation reaction between an analine and a bromo oxocycloalkanecarboxylate as illustrated in Scheme 3 below:

Scheme 3

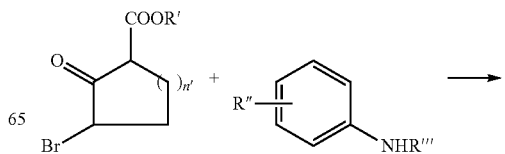

-continued

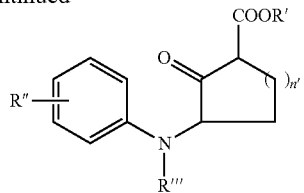

In the above scheme R' is an $R^3$ group as defined herein, R" is an $R^1$ and/or an $R^2$ group as defined herein, R'" is an $R^6$ group as defined herein and n' is an integer of 1-3.

In another aspect, the present invention provides a pharmaceutical composition comprising the composition of the invention together with a biocompatible carrier suitable for mammalian administration.

In another aspect, the present invention provides a pharmaceutical composition comprising the composition of the invention together with a biocompatible carrier suitable for mammalian administration.

The "biocompatible carrier" is a fluid, especially a liquid, in which the composition of the invention is suspended or dissolved, such that the pharmaceutical composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). The biocompatible carrier may also comprise biocompatible organic solvents such as ethanol. Such organic solvents are useful to solubilise more lipophilic compounds or formulations. In an embodiment, the biocompatible carrier is pyrogen-free water for injection, isotonic saline or an aqueous ethanol solution. The pH of the biocompatible carrier for intravenous injection is suitably in the range 4.0 to 10.5.

In a yet further aspect, the present invention provides for use of the pharmaceutical composition of the invention in a medical method, wherein said medical method is more particularly either a method for treatment or a method for diagnosis of a pathological condition. In particular, the pharmaceutical composition of embodiments of the present invention is useful in the treatment or diagnosis of a pathological condition comprising inflammation.

Where the composition of embodiments of the invention is an in vivo imaging composition as referred to above, i.e. wherein $R^6$ comprises [$^{18}$F]fluoro, the medical method is more particularly a method of in vivo imaging comprising:
  administering said pharmaceutical composition to a subject;
  detecting signals emitted by the [$^{18}$F]fluoro comprised in said pharmaceutical composition; and
  generating an image representative of the location and/or amount of said signals.

The "subject" of the invention can be any human or animal subject. In an embodiment, the subject of the invention is a mammal. More particularly, said subject is an intact mammalian body in vivo. In an embodiment, the subject is a human.

"Administering" the in this in vivo imaging method is more particularly carried out parenterally, and more particularly intravenously.

The "detecting" step of the method of the invention involves detection of signals emitted by the [$^{18}$F]fluoro by means of a detector sensitive to said signals, i.e. a positron-emission tomography (PET) detector.

The "generating" step of the method of the invention is carried out by a computer which applies a reconstruction algorithm to the acquired signal data to yield a dataset. This dataset is then manipulated to generate images showing the location and/or amount of signals emitted by said [$^{18}$F]fluoro.

The in vivo imaging composition of the invention is readily obtained by reaction with [$^{18}$F]fluoride of a precursor composition as defined above, i.e. a composition of the invention wherein $R^6$ comprises a leaving group as defined hereinabove. [$^{18}$F]-fluoride ion ($^{18}F\overline{O}$) is normally obtained as an aqueous solution from the nuclear reaction $^{18}O(p,n)^{18}F$ and is made reactive by the addition of a cationic counterion and the subsequent removal of water. Removal of water is commonly carried out by application of heat and use of a solvent such as acetonitrile to provide a lower boiling azeotrope. A "cationic counterion" is a positively-charged counterion examples of which include large but soft metal ions such as rubidium or caesium, potassium complexed with a cryptand, or tetraalkylammonium salts. In an embodiment, the cationic counterion is a metal complex of a cryptand, more particularly wherein said metal is potassium and wherein said cryptand is Kryptofix 222.

In another aspect the present invention provides the pharmaceutical composition of the invention for use in any of the above-defined medical methods.

In a yet further aspect, the present invention provides for use of the composition of the invention in the manufacture of the pharmaceutical composition of the invention for use in any of the above-defined medical methods.

In a further aspect the present invention provides a kit suitable for making the in vivo imaging composition of the invention, wherein said kit comprises said precursor composition. A specialised kit, or "cassette", may be used to prepare the in vivo imaging composition of the present invention on an automated radiosynthesis apparatus. By the term "cassette" is meant a piece of apparatus designed to fit removably and interchangeably onto an automated radiosynthesis apparatus, in such a way that mechanical movement of moving parts of the synthesizer controls the operation of the cassette from outside the cassette, i.e. externally. [$^{81}$F]-radiotracers are now often conveniently prepared on automated radiosynthesis apparatuses. By the term "automated radiosynthesis apparatus" is meant an automated module based on the principle of unit operations as described by Satyamurthy et at (1999 Clin Positr Imag; 2(5): 233-253). The term "unit operations" means that complex processes are reduced to a series of simple operations or reactions, which can be applied to a range of materials. Such automated radiosynthesis apparatuses are commercially available from a range of suppliers (Satyamurthy et al, above), including: GE Healthcare; CTI Inc; Ion Beam Applications S. A. (Chemin du Cyclotron 3, B-1348 Louvain-La-Neuve, Belgium); Raytest (Germany) and Bioscan (USA).

A commercial automated radiosynthesis apparatus also provides suitable containers for the liquid radioactive waste generated as a result of the radio synthesis. Automated radiosynthesis apparatuses are not typically provided with radiation shielding, since they are designed to be employed in a suitably configured radioactive work cell. The radioactive work cell provides suitable radiation shielding to protect the operator from potential radiation dose, as well as ventilation to remove chemical and/or radioactive vapours. Suitable cassettes comprise a linear array of valves, each linked to a port where reagents or vials can be attached, by either needle puncture of an inverted septum-sealed vial, or by gas-tight, marrying joints. Each valve has a male-female joint which interfaces with a corresponding moving arm of the automated radiosynthesis apparatus. External rotation of the arm thus controls the opening or closing of the valve when the cassette is attached to the automated radiosynthesis apparatus. Additional moving parts of the automated radiosynthesis apparatus are designed to clip onto syringe plunger tips, and thus raise or depress syringe barrels.

The cassette is versatile, and, in an embodiment, having several positions where reagents can be attached, and several suitable for attachment of syringe vials of reagents or chromatography cartridges (e.g. for SPE). The cassette always comprises a reaction vessel. Such reaction vessels are, in an embodiment, 0.5 to 10 mL, more particularly 0.5 to 5 mL, and more particularly 0.5 to 4 mL in volume and are configured such that 3 or more ports of the cassette are connected thereto, to permit transfer of reagents or solvents from various ports on the cassette. In an embodiment, the cassette has 15 to 40 valves in a linear array, more particularly 20 to 30, with 25 being preferred in an embodiment. The valves of the cassette are in an embodiment each identical, and in an embodiment are 3-way valves. The cassettes are designed to be suitable for radiopharmaceutical manufacture and are therefore manufactured from materials which are of pharmaceutical grade and ideally also are resistant to radiolysis.

Automated radiosynthesis apparatuses of embodiments of the present invention comprise a disposable or single use cassette which comprises all the reagents, reaction vessels and apparatus necessary to carry out the preparation of a given batch of the in vivo imaging composition of embodiments of the invention.

The following non-limiting examples serve to illustrate embodiments of the invention in more detail.

BRIEF DESCRIPTION OF THE EXAMPLES

Example 1 describes a method to obtain a composition comprising a compound of Formula I as defined herein and a compound of Formula II as defined herein, wherein a prior art method is compared with the method of the present invention.

List of Abbreviations Used in the Examples

OMs: mesylate

Example 1: Synthesis of N,N-diethyl-9-(2-[$^{18}$F]fluoroethyl)-5-methoxy-2,3,4,9-tetrahydro-1H-carbazole-4-carboxamide The compound N,N-diethyl-9-(2-[$^{18}$F]fluoroethyl)-5-methoxy-2,3,4,9-tetrahydro-1H-carbazole-4-carboxamide was synthesised using the following steps:

Step 1: Synthesis of ethyl 3-bromo-2-oxocyclohexanecarboxylate

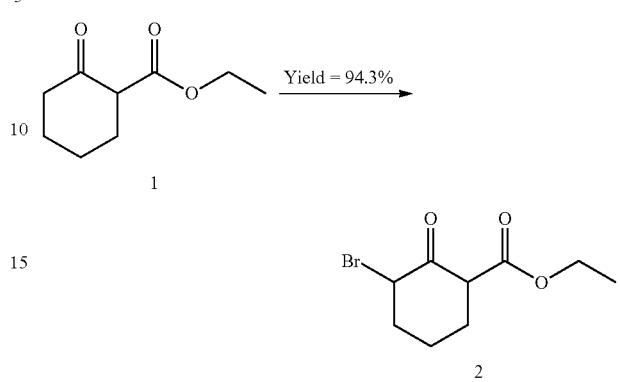

Step 2: Synthesis of N-(2-(benzyloxy)ethyl)-2-chloro-5-methoxyaniline

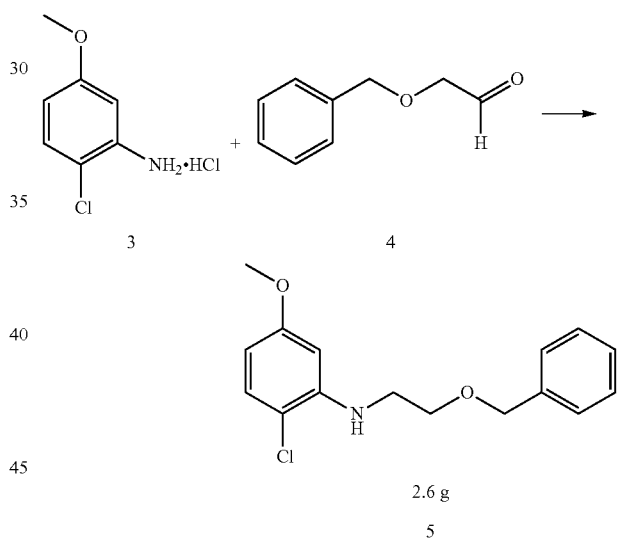

Step 3: Synthesis of ethyl 3-((2-(benzyloxy)ethyl)(2-chloro-5-methoxyphenyl)amino)-2-hydroxycyclohex-1-enecarboxylate

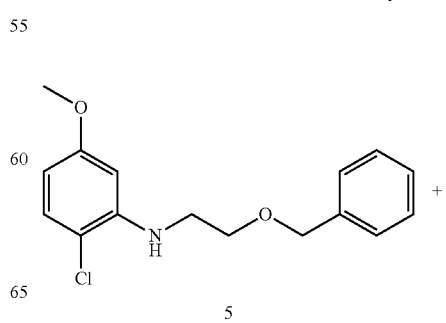

-continued
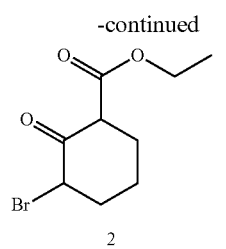
2
Step 5: Synthesis of 9-(2-(benzyloxy)ethyl)-8-chloro-5-methoxy-2,3,4,9-tetrahydro-1H-carbazole-4-carboxylic Acid
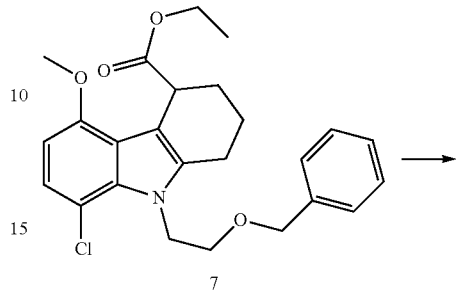
7
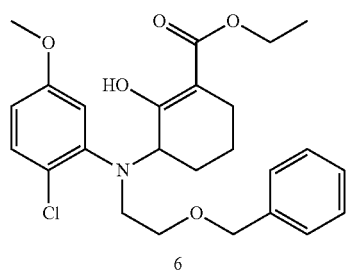
6
Step 4: Synthesis of ethyl 9-(2-(benzyloxy)ethyl)-8-chloro-5-methoxy-2,3,4,9-tetrahydro-1H-carbazole-4-carboxylate
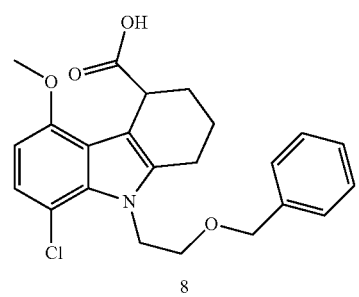
8
Step 6: Synthesis of 9-(2-(benzyloxy)ethyl)-8-chloro-5-methoxy-2,3,4,9-tetrahydro-1H-carbazole-4-carbonyl Chloride
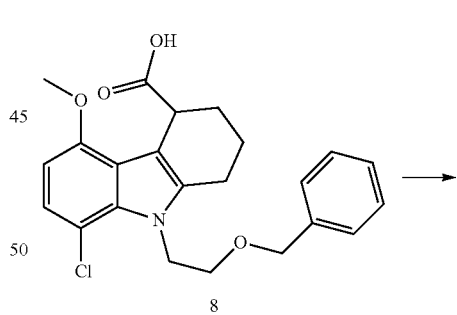
6
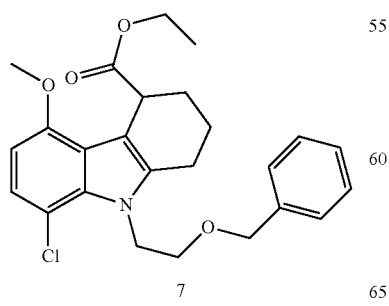
7
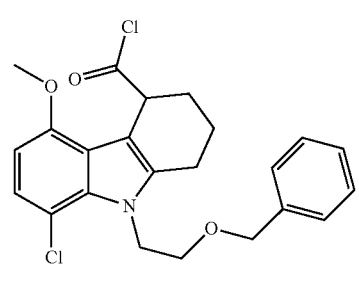
8
9

15

Step 7: Synthesis of 9-(2-(benzyloxy)ethyl)-8-chloro-N,N-diethyl-5-methoxy-2,3,4,9-tetrahydro-1H-carbazole-4-carboxamide

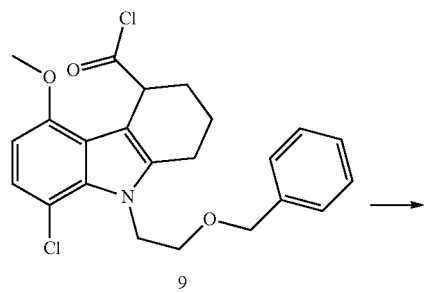

9

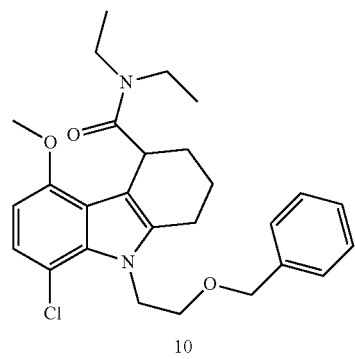

10

Step 8: Synthesis of 9-(2-(benzyloxy)ethyl)-N,N-diethyl-5-methoxy-2,3,4,9-tetrahydro-1H-carbazole-4-carboxamide

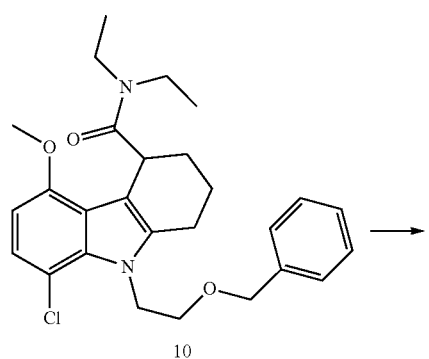

10

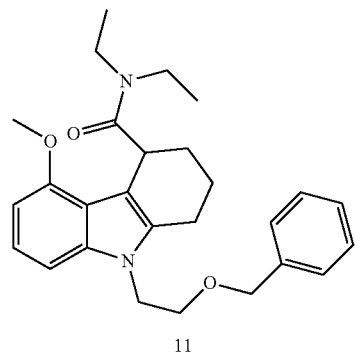

11

16

Step 9: Synthesis of N,N-diethyl-9-(2-hydroxyethyl)-5-methoxy-2,3,4,9-tetrahydro-1H-carbazole-4-carboxamide

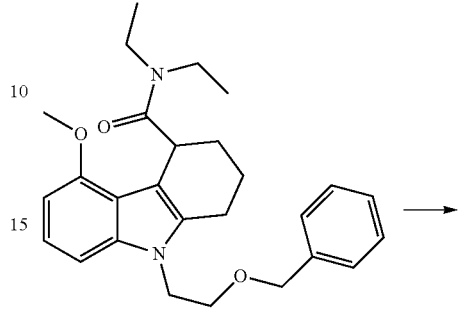

11

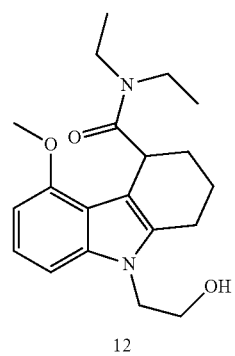

12

Step 10: Synthesis of 2-(4-(diethylcarbamoyl)-5-methoxy-3,4-dihydro-1H-carbazol-9(2H)-yl)ethyl methanesulfonate

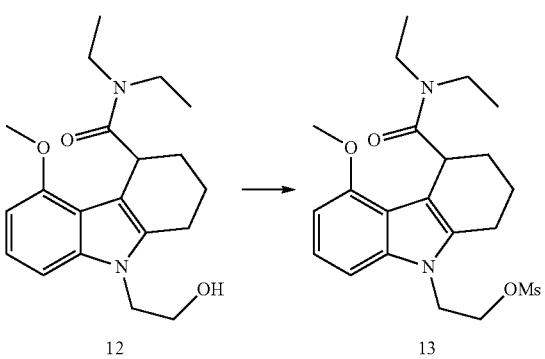 [SMILES: CCN(CC)C(=O)C1CCCc2c1c1c(OC)cccc1n2CCO ; CCN(CC)C(=O)C1CCCc2c1c1c(OC)cccc1n2CCOS(C)(=O)=O]

12               13

Step 11: Synthesis of N,N-diethyl-9-(2-[$^{18}$F]fluoro-ethyl)-5-methoxy-2,3,4,9-tetrahydro-1H-carbazole-4-carboxamide

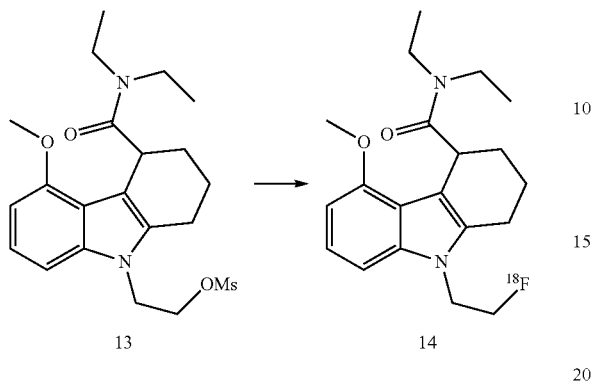

In the prior art method (Wadsworth et at WO 2010/109007 Example 1), intermediate 10 above was purified by crystallization from diethyl ether (Wadsworth et at WO 2010/109007 Example 1(i)). The method of embodiments of the present invention was carried out as generally described by Wadsworth et at (WO 2010/109007). However, in the method of embodiments of the present invention, intermediate 10 was purified by crystallization from diethyl ether in the presence of diethyl amine.

TABLE 1 shows the percent yield of the desired product along with the amount of incorrect isomer impurity (where measured) in brackets thereafter. With the method of the invention it can be seen that the amount of the incorrect isomer in intermediate 10, which was purified using the method of the invention was only 0.2%.

| Intermediate | 6 | 7 | 8 | 10 | 12 | 13 |
|---|---|---|---|---|---|---|
| Prior Art | 95.10 | 78.20 (6.4) | 90.40 (7.6) | 92.18 (7.0) | 93.15 (4.9) | 91.75 (5.1) |
| Prior Art | 91.28 | 77.97 (6.9) | 82 (9.0) | 95.40 (3.2) | 91.10 (3.3) | 92.87 (2.3) |
| Invention | 95.00 | 84.00 (6.5) | 87.27 (5.8) | 97.92 (0.2) | — | — |

What is claimed is:

1. A method of obtaining a composition comprising a compound of Formula Ia:

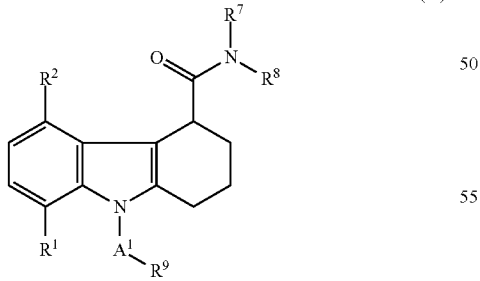

wherein:
   $R^1$ is a halogen;
   $R^2$ is $C_{1-3}$ alkoxy;
   $R^7$ and $R^8$ are $C_{1-6}$ alkyl; and
   $A^1$ is a bond or $C_{1-10}$ alkylene, and $R^9$ is a leaving group, or $R^9$ is the group —O—$R^{10}$ wherein $R^{10}$ is hydrogen, $C_{1-3}$ alkyl, $C_{3-6}$ aryl, $C_{7-10}$ arylalkyl, or a hydroxyl protecting group, wherein said composition comprises no more than 1% of a compound of Formula IIa:

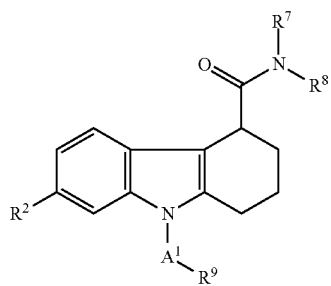

wherein each of $R^2$, $R^7$, $R^8$, $R^9$ and $A^1$ are as defined for Formula Ia, the method comprising:
crystallizing the composition from an organic solvent in the presence of the catalytic amount of N,N-diisopropyl ethylamine, triethyl amine, or diethyl amine to obtain said composition, wherein the composition comprises the compound of Formula Ia and no more than 1% of the compound of Formula IIa as a by-product.

2. The method of claim 1, wherein said organic base is selected from N,N-diisopropyl ethylamine or diethylamine.

3. The method of claim 1, wherein:
$R^1$ is halogen;
$R^2$ is methoxy;
$R^7$ and $R^8$ are $C_{1-3}$ alkyl;
$R^9$ is benzyloxy; and
$A^1$ is $C_{1-3}$ alkylene.

4. The method of claim 1, wherein the composition comprises no more than 0.5% of the compound of Formula IIa.

5. The composition resulting from the method of claim 1, wherein $R^9$ is a leaving group.

* * * * *